United States Patent [19]
Fukusumi et al.

[11] Patent Number: 6,111,076
[45] Date of Patent: Aug. 29, 2000

[54] HUMAN G-PROTEIN COUPLED RECEPTOR (HIBCD07)

[75] Inventors: Shoji Fukusumi; Shuji Hinuma; Ryo Fujii, all of Ibaraki, Japan

[73] Assignee: Takeda Chemical Industries, Ltd., Osaka, Japan

[21] Appl. No.: 09/163,669

[22] Filed: Sep. 30, 1998

Related U.S. Application Data

[62] Division of application No. 08/852,806, May 7, 1997, Pat. No. 5,874,245.
[60] Provisional application No. 60/017,915, May 16, 1996.

[51] Int. Cl.$^7$ .................................................. C07K 14/705
[52] U.S. Cl. ............................................ 530/350; 530/324
[58] Field of Search ...................................... 530/350, 324

[56] References Cited

FOREIGN PATENT DOCUMENTS 0 643 076 A1  3/1995  European Pat. Off. .

OTHER PUBLICATIONS

Nambi Aiyar, et al., "A cDNA Encoding the Calcitonin Gene–related Peptide Type 1 Receptor", The Journal of Biological Chemistry, 271(19):11325–11329 (1996).
GenBank Accession #R61167.
GenBank Accession #H46133.
GenBank Accession #Z44961.
EST #55423.
George et al. "Current Methods in Sequence Comparison and Analysis", Macromolecular Sequencing and Synthesis Selected Methods and Applications, Chapter 12, pp. 127–149 (1988).
Perrin et al. "Identification of a second corticotropin–releasing factor receptor gene and characterization of a cDNA expressed in heart", Proc. Natl. Acad. Sci., vol. 92, pp. 2969–2973 (1995).

*Primary Examiner*—John Ulm
*Attorney, Agent, or Firm*—William T. Han; Ratner & Prestia; William T. King

[57] ABSTRACT

Human G-protein coupled receptor polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the G-protein coupled receptor polypeptides, respectively. Also disclosed are diagnostic methods for detecting a mutation in the G-protein coupled receptor nucleic acid sequences and an altered level of the soluble form of the receptors.

7 Claims, 9 Drawing Sheets

```
1351  TTCATAAAT  CTGAACGCTC  CATCATCTTG  CTGAACTTCT  GCCTGTCCAT  1400
1351  TTCATAAAT  CTGAACGCTC  CATCATCTTG  CTGAACTTCT  GCCTGTCCAT  1400

1401  CTTGGCATCC  AACATCCTGA  TCCTCGTGGG  CCAGTCCCGG  GTGCTGAGCA  1450
1401  CTTGGCATCC  AACATCCTGA  TCCTCGTGGG  CCAGTCCCGG  GTGCTGAGCA  1450

1451  AGG-------  ----------  ----------  ----------  ----------  1500
1451  AGGGCGTGTG  CACCATGACG  GCTGCCTTCC  TGCACTTCCT  CCTTCTCTCC  1500

1501  ----------  ----------  ----------  ----------  ----------  1550
1501  TCCTTTTGCT  GGGTGCTTAC  CGAGGCCTGG  CAGTCCTACC  TGGCTGTCAT  1550

1551  ----------  ----------  ----------  ----------  ----------  1600
1551  TGGGCGGATG  CGCACCCGCC  TCGTTCGCAA  GCGCTTCCTC  TGCCTGGGCT  1600

1601  ----TCTGCC  TGCCCTGGTG  GTGGCCGTGT  CTGTTGGCTT  TACCCGAACG  1650
1601  GGGTCTGCC  TGCCCTGGTG  GTGGCCGTGT  CTGTTGGCTT  TACCCGAACG  1650
```

FIG. 2

```
  1 CAACAGCGCAGCCGGAAGTGCAGCGTGGCGGGCCCAGCCTGGGCCACATGCACGGGTGCC    60
  1                                                                1

61 CTCACTGACACCCGGGAGTGCAGCAACCTCGAGTGCCCGGCCACTGATAGCAAGTGGGGG   120
  1                                                                1

121 CCATGGAATGCCTGGAGCCTGTGCTCTAAGACGTGTGACACAGGCTGGCAGCGCCGCTTC   180
  1                                                                1

181 CGCATGTGCCAGGCCACGGGCACGCAGGGCTACCCCTGCGAGGGCACCGGAGAGGAGGTG   240
  1    M  C  Q  A  T  G  T  Q  G  Y  P  C  E  G  T  G  E  E  V    19

241 AAGCCTTGTAGTGAGAAGAGGTGTCCAGCCTTCCATGAGATGTGCAGGGATGAGTACGTG   300
 19  K  P  C  S  E  K  R  C  P  A  F  H  E  M  C  R  D  E  Y  V   39

301 ATGCTGATGACGTGGAAGAAGGCAGCTGCTGGCGAGATCATCTACAACAAGTGCCCCCCG   360
 39  M  L  M  T  W  K  K  A  A  A  G  E  I  I  Y  N  K  C  P  P   59

361 AATGCCTCAGGGTCTGCCAGCCGCCGCTGTCTCCTCAGTGCCCAAGGCGTGGCGTACTGG   420
 59  N  A  S  G  S  A  S  R  R  C  L  L  S  A  Q  G  V  A  Y  W   79

421 GGGCTGCCCAGCTTTGCTCGCTGCATCTCCCATGAGTACCGCTACCTGTATCTGTCACTT   480
 79  G  L  P  S  F  A  R  C  I  S  H  E  Y  R  Y  L  Y  L  S  L   99

481 AGGGAGCACCTGGCCAAGGGGCAGCGCATGCTGGCAGGCGAGGGCATGTCGCAGGTGGTG   540
 99  R  E  H  L  A  K  G  Q  R  M  L  A  G  E  G  M  S  Q  V  V  119

541 CGCAGCCTGCAGGAGCTACTGGCCCGGCGCACCTACTATAGTGGGGACCTGCTCTTCTCT   600
119  R  S  L  Q  E  L  L  A  R  R  T  Y  Y  S  G  D  L  L  F  S  139

601 GTGGACATTCTGAGGAATGTCACTGACACCTTTAAGAGGGCCACCTACGTGCCCTCGGCT   660
139  V  D  I  L  R  N  V  T  D  T  F  K  R  A  T  Y  V  P  S  A  159
```

Sequence around the 5' end of HIBCD07 as
revealed by 5' RACE.

▼  indicates the 5' end of each 5' RACE product, and
▭  indicates the expected initiation codon ATG.

TAK50002 Sequence of HIBCD07 and corresponding amino acid sequence

```
  1  TGTGACACAGGCTGGCAGCCGCTTCCGGCTTCCGCATGCCAGGCCACGGGCCACGCAGGCTAC              60
  1                        MetCysGlnAlaThrGlyThrGlnGlyTyr                        10

61  CCCTGCGAGGGCACCGGAGAGGAGGTGAAGCCTTGTAGTGAGAAGAGGTGTCCAGCCTTC             120
 10  ProCysGluGlyThrGlyGluGluValLysProCysSerGluLysArgCysProAlaPhe              30

121  CATGAGATGTGCAGGGATGAGTACGTGATGCTGATGACGTGGAAGAAGGCAGCTGCTGGC             180
 30  HisGluMetCysArgAspGluTyrValMetLeuMetThrTrpLysLysAlaAlaAlaGly              50

181  GAGATCATCTACAACAAGTGCCCCCGAATGCCTCAGGGTCTGCAGCCGCTGCAGCTGTCTC            240
 50  GluIleIleTyrAsnLysCysProProAsnAlaSerGlySerAlaSerArgArgCysLeu              70

241  CTCAGTGCCCAAGGCGTGGCTGTACTGGGGCTGCCCAGTTTGCTCGCTGCATCTCCCAT             300
 70  LeuSerAlaGlnGlyValAlaTyrTrpGlyLeuProSerPheAlaArgCysIleSerHis              90

301  GAGTACGCTACTGTATCTGTCACTTAGGGAGCACCTGGCCAAGGCACTGGCAGGCATGCTG            360
 90  GluTyrArgTyrLeuTyrLeuSerLeuArgGluHisLeuAlaLysAlaLysGlyGlnArgMetLeu       110

361  GCAGGGGAGGGCATGTCCAGGTGTGCCAGCCTGAGAGAGCTGGAGCTGGAACTAAGAAGGACT          420
110  AlaGlyGluGlyMetSerGlnValValArgSerLeuGlnGluLeuGluLeuLeuAlaArgArgThr       130

421  TACTATAGTGGGGACCTGTCTCTGTGACATTCTGAGGAATGCATTCACTGACACCTTT              480
130  TyrTyrSerGlyAspLeuSerLeuPheSerValAspIleLeuLeuArgAsnValThrAspThrPhe       150

481  AAGAGGGCCACCTACGTGCCCTGGCTGATGATGTGCAGGCTTCTTCCAGGTGGTGAGC              540
150  LysArgAlaThrTyrValProSerAlaAspValGlnArgPhePheGlnValValSer               170

541  TTCATGTGTGATGCGGAAAAACAAGGAGAAGTGGGACGATGCTCAGCAGGTGTCCCCTGGC            600
170  PheMetValAspAlaGluAsnLysGluLysTrpAspAspAlaGlnGlnValSerProGly             190

601  TCTGTGCACCTGCTCCGTGTGTGTGAGGACTTCATTCACCTGGTGGGGCGATGCTCTCAAG            660
190  SerValHisLeuLeuArgValValGluValGlnAspPheIleHisLeuValGlyAspAlaLeuLys       210

661  GCCTTCCAGAGCTCTCTGATTGTCACAGATAATCTACAGCATTCAGCGAGAGCCC                  720
210  AlaPheGlnSerSerLeuIleValThrAspAsnLeuValIleSerLeuIleArgGluPro             230
```

FIG. 4B

| | | |
|---|---|---|
| 721 | GTCTCAGCTGTGTCAGTGACATCACGTTCCCATGGGGCCGCGGGGCATGAAGGAC | 780 |
| 230 | ValSerAlaValSerAspIleThrPheProMetArgGlyArgArgGlyMetLysAsp | 250 |
| 781 | TGGGTGCGGCACTCAGAGACCGCCTCTTCCTGCCAAGGAGGTGCTCAGCCTCTCC | 840 |
| 250 | TrpValArgHisSerGluAspArgLeuPheLeuProLysGluValLeuSerLeuSer | 270 |
| 841 | CCAGGGAAGCCAGCCACATCGGGCCAGCAGCCCTGGCAGGGGAGGGCCCAGGA | 900 |
| 270 | ProGlyLysProAlaThrSerGlyAlaAlaGlySerProGlyArgGlyArgGlyProGly | 290 |
| 901 | ACGGTGCCTCCTGCCCAGGCCACTCCCACAGGCCTCCTCCAGAGACCCTGATGAG | 960 |
| 290 | ThrValProProGlyHisSerHisGlnArgLeuLeuProAlaAspProAspGlu | 310 |
| 961 | TCCTCCTACTTTGTGATCGTGCTGTACTCTACGCACCCTGGCCTCATCCTGCCT | 1020 |
| 310 | SerSerTyrPheValIleValLeuTyrArgThrLeuGlyLeuIleLeuProPro | 330 |
| 1021 | CCCAGGCCCCCGCTGGCCCTGAGCCTCACATCCGGGTGATGACAGTGCGCCCCTACC | 1080 |
| 330 | ProArgProProLeuAlaLeuSerLeuHisIleArgValMetThrValArgProThr | 350 |
| 1081 | CAGCCTCCAGTGGCCCTCATCACTGTGGAGCTCTCCTACATCATCGAACATGGACCACG | 1140 |
| 350 | GlnProProValAlaLeuIleThrValGluLeuSerTyrIleIleAsnGlyThrThr | 370 |
| 1141 | GATCCCCATTGCGCCAGCTACTCCAGAGACGATGCCAGCTCAGGAGACTGGGAC | 1200 |
| 370 | AspProHisCysAlaSerTyrSerArgAlaAspAlaSerSerGlyAspTrpAsp | 390 |
| 1201 | ACTGAAAATTGCCAGACCCTGGAGACCCTGCAGCTCACACCCGCTGCCAGTGCCACAC | 1260 |
| 390 | ThrGluAsnCysGlnThrLeuGluThrLeuGlnAlaAlaHisThrArgCysGlnHis | 410 |
| 1261 | CTGTCCACCTTGCTGTACTAGCCCAAGGACCTGACCCTGAGCTGGCGGGC | 1320 |
| 410 | LeuSerThrPheAlaValLeuAlaGlnProProLysAspLeuThrLeuGluLeuAlaGly | 430 |
| 1321 | TCCCCCTGGTCCCCTGGTGATGGCGTGCAGTGCGTGCGTCGTCAGTGTGCATGGGCCCTG | 1380 |
| 430 | SerProSerValProLeuValIleGlyCysAlaValSerCysMetAlaLeuLeuThrLeu | 450 |

FIG. 4C

```
1381 CTCGCCATCTATGCGGCCTTTGGAGGTTCATAAATCTGAACGCTCCATCATCTTGCTG      1440
 450 LeuAlaIleTyrAlaAlaPheTrpArgPheIleLysSerGluArgSerIleIleLeuLeu     470

1441 AACTTCTGCCTGTCCATCTTGGCATCCAACATCCTGATCCTGGTGGGCCAGTCCGGGTG      1500
 470 AsnPheCysLeuSerIleLeuAlaSerAsnIleLeuIleLeuValGlyGlnSerArgVal     490

1501 CTGAGCAAGGGCGTGTGCACCATGACGGCTGCCTTCCTGCACTCTTCTTCTTCCTCC        1560
 490 LeuSerLysGlyValCysThrMetThrAlaAlaPheLeuHisPhePhePheLeuSerSer     510

1561 TTTGCTGGGTGCTTACCGAGCCTGGCAGTCCTACCTGGCTGTCATTGGGCGATGCGC        1620
 510 PheCysTrpValLeuThrGluAlaTrpGlnSerTyrLeuAlaValIleGlyArgMetArg     530

1621 ACCCGCCTCGTTGCAAGGGCTTCCTGCCTCGGGTCTCGCTGGGTCTGCCCTGGTG          1680
 530 ThrArgLeuValArgLysArgPheLeuCysLeuGlyTrpGlyLeuProAlaLeuValVal     550

1681 GCCGTGTCTGTTGGCTTTACCGAAGGATACGGTACATCCAGTCTACTGCTGCTC            1740
 550 AlaValSerValGlyPheThrArgThrLysGlyTyrGlyTyrSerSerTyrCysTrpLeu     570

1741 TCCCTGAGGGCGGCCTGCTCCTAGCGCTTGTGGCCCTTGCAGCCGTCATTGTCCTGGTG      1800
 570 SerLeuGluGlyGlyLeuLeuTyrAlaPheValGlyProAlaAlaIleValLeuVal       590

1801 AACATGCTCATCGAATCGTCTTCAACAGTCTTGAATTGGCTCATGGCATTCCGAC           1860
 590 AsnMetLeuIleIleGlyIleValPheAsnLysLeuMetAlaArgAspGlyIleSerAsp     610

1861 AAATCCAAGAAGCAGAGGGCCCTCACTCTTGAGCTCTGGTGGTGTCGTTGCCCCTG         1920
 610 LysSerLysLysGlnArgAlaGlyAlaSerLeuTrpSerSerCysValValLeuProLeu    630

1921 CTGGGGCTCACCTGATGTCCTGGCTATGACAGACCCGTTCCGTCCTCCTTC              1980
 630 LeuAlaLeuThrTrpMetSerAlaLeuAlaMetThrAspArgArgSerValLeuPhe       650

1981 CAGGCCCTCTTTGCTGTCTTCAACTCCGGCAGGCTTTGTCATCACTGCTGTGCACTGC      2040
 650 GlnAlaLeuPheAlaValPheAsnSerAlaGlnGlyPheValIleThrAlaValHisCys    670
```

FIG. 4D

```
2041 TTCCTGCGCCGAGAGGTCCAGGATGTGGTGAAGTGCCAGATGGGGGTGTGCCGGGCTGAT    2100
 670 PheLeuArgArgGluValGlnValValLysCysGlnMetGlyValCysArgAlaAsp       690

2101 GAGAGGCGAAGACTCCCTGACTCGTGTAAGAACGGGCAGCTGCAGATCCTGTCAGACTTT    2160
 690 GluSerGluAspSerProAspSerCysLysAsnGlyGlnLeuGlnIleLeuSerAspPhe    710

2161 GAAAAGGATGTGGATCTGCTTGTCAAACAGTGTCTTCAAGGAGGTCAACACTTGCAAC      2220
 710 GluLysAspValAspLeuLeuValLysGlnThrValLeuPheLysGluValAsnThrCysAsn 730

2221 CGTCCACCATCACGGGCACACTATCCGTGTCCTGGATGATGAGGAGCCCAAG            2280
 730 ProSerThrIleThrGlyThrLeuSerArgLeuSerLeuAspGluGluProLys          750

2281 TCCTGCCTCGTGGGCCCTGAGGGCAGCCTCAGCTTCTCACCACTGCCTGGAATATCCTG    2340
 750 SerCysLeuValGlyProGluGlySerLeuSerPheSerProLeuProGlyAsnIleLeu    770

2341 GTGCCCATGGCAGCTCCAGGGCTGGGGGAGCCTCGCGGCCCCACAGAGAGGCCAACCCT     2400
 770 ValProMetAlaAlaSerProGlyLeuGlyGluProProProGlnGluAlaAsnPro       790

2401 GTTTACATGTGTGGGCTGGGTGGCCTGGAGGAGCCTGGACCTCACATGGCTGGGCCACT    2460
 790 ValTyrMetCysGlyGlyGlyGlyLeuArgGlnLeuAspLeuThrTrpLeuArgProThr    810

2461 GAGCCAGGCTCTGAGGAGACTACATGTGCTGCCCGGGACTTTGAGCTGCAGCCT          2520
 810 GluProGlySerGluGluAspTyrMetValLeuProArgArgThrLeuSerLeuGlnPro    830

2521 GGCGGTGGGGGTGGAGGTGGTGGAGGATGCCGAGGAGCCCGGCCCCGAGGGGACCCCGG    2580
 830 GlyGlyGlyGlyGlyGlyGlyGlyGluAspAlaProArgAlaArgProGlyThrProArg   850

2581 CGAGCTGCCAAGACAGCTACCCACTGAAGGCTACCCCAGCTTCCTGTCCGTGACCAC      2640
 850 ArgAlaAlaLysThrValAlaHisThrGluGlyTyrProSerPheLeuSerValAspHis    870

2641 TCGGGCCTGGGGCTGGGGCCTGCCTATGGATCTCTCCAGAATCCCTATGAATGACCTTC    2700
 870 SerGlyLeuGlyLeuGlyProAlaTyrGlySerLeuGlnAsnProTyrGlyMetThrPhe    890

2701 CAACCGGCACCGCCCGACACCCAGCGGCCCGCCAAGTGCCCGAGCCAGGGAGGCGCAGCCGG 2760
```

```
 890           GlnProProProThrProSerAlaArgGlnValProGluProGlyGluArgSerArg              910
2761 ACCATGCCTCGCACCGTGCCCGGCTCTACCGAAGATGGGCTCCCTGAGCGAAAGAAA                         2820
 910 ThrMetProArgThrValProGlySerThrMetGlySerLeuArgGluArgLysLys                         930
2821 TTACGGTATTCAGACCTTGAGAAGGTGATGCACACCCGAAACGGCATTCAGAA                             2880
 930 LeuArgTyrSerAspLeuAspPheGluLysValMetHisThrArgLysArgHisSerGlu                      950
2881 CTCTACCAGAGCTCAACCAGAAGTTCCACACTTTCGACCGCTACCGCAGCCAGTCCACG                       2940
 950 LeuTyrHisGluLeuAsnGlnLysPheHisThrPheAspArgTyrArgSerGlnSerThr                      970
2941 GCCAAGAGGAGAAGCGGTGAGTGTCCTCGGGTGGGGCCGAGCGAGCGTGTGC                              3000
 970 AlaLysArgGluGluLysArgTrpSerValSerSerGlyGlyAlaAlaGluArgSerValCys                   990
3001 ACCGATAAGCCCAGCCCCCAGTTGTCCCAACATCGGCGCCATCAGAGC                                  3060
 990 ThrAspLysProSerProGlyGluArgProSerLeuSerGlnHisArgArgHisGlnSer                     1010
3061 TGGAGCACCTTCAAATCTATGACACTGGCCTCGCCCCCAAGCCCCGAGAACGGCTG                          3120
1010 TrpSerThrPheLysSerMetThrLeuGlySerLeuProProLysProArgGluArgLeu                     1030
3121 ACTCTGCACGGGCAGCAGCCTGGAGCCCACAGAACCACCGGATGTGACTTCCAGACA                         3180
1030 ThrLeuHisArgAlaAlaAlaAlaTrpGluProThrGluProProThrProProAspPheGlnThr               1050
3181 GAGGTGTGAGTGCCACGCTGGACTGCCCACTGCATATAAATATATATATCTCTATTT                         3240
1050 GluVal***                                                                        1053
3241 CACACTCCACTTTGAACTACCAGGAGCCA                                                     3271
                                                                                      1053
```

FIG. 4E

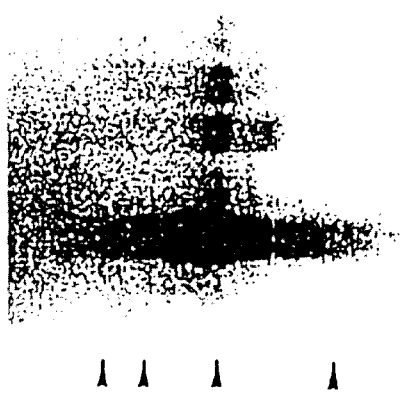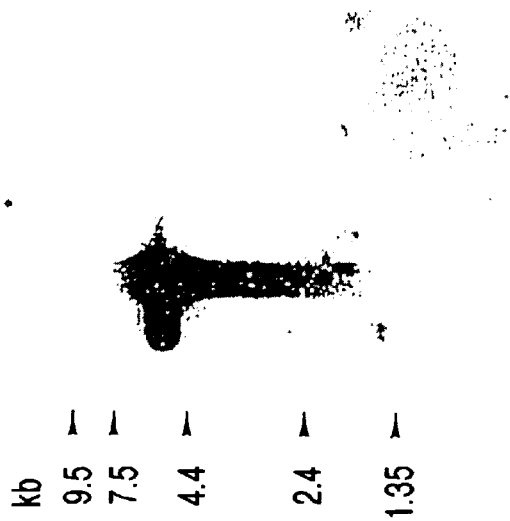
FIG. 5

HUMAN G-PROTEIN COUPLED RECEPTOR (HIBCD07)

RELATED APPLICATION

This application is a division of application No. 08/852,806, filed May 7, 1997, now U.S. Pat. No. 5,874,245, which claims the benefit of U.S. Provisional Application No. 60/017,915, filed May 16, 1996.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention are human 7-transmembrane receptors. The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

SUMMARY OF THE INVENTION

In accordance with one aspect of the present invention, there are provided novel polypeptides as well as biologically active and diagnostically or therapeutically useful fragments and derivatives thereof. The polypeptides of the present invention are of human origin.

In accordance with another aspect of the present invention, there are provided isolated nucleic acid molecules encoding the polypeptide of the present invention including mRNAs, DNAs, cDNAs, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said polypeptide and subsequent recovery of said polypeptide.

In accordance with yet a further aspect of the present invention, there are provided antibodies against such polypeptides.

In accordance with another aspect of the present invention there are provided methods of screening for compounds which bind to and activate or inhibit activation of the receptor polypeptides of the present invention and for receptor ligands.

In accordance with still another embodiment of the present invention there is provided a process of using such activating compounds to stimulate the receptor polypeptide of the present invention for the treatment of conditions related to the under-expression of the G-protein coupled receptors.

In accordance with another aspect of the present invention there is provided a process of using such inhibiting compounds for treating conditions associated with over-expression of the G-protein coupled receptors.

In accordance with yet another aspect of the present invention there is provided non-naturally occurring synthetic, isolated and/or recombinant G-protein coupled receptor polypeptides which are fragments, consensus fragments and/or sequences having conservative amino acid substitutions, of at least one transmembrane domain of the G-protein coupled receptor of the present invention, such that the receptor may bind G-protein coupled receptor ligands, or which may also modulate, quantitatively or qualitatively, G-protein coupled receptor ligand binding.

In accordance with still another aspect of the present invention there are provided synthetic or recombinant G-protein coupled receptor polypeptides, conservative substitution and derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-protein coupled receptors or fragments thereof, as receptor types and sub-types.

In accordance with yet a further aspect of the present invention, there is also provided diagnostic probes comprising nucleic acid molecules of sufficient length to specifically hybridize to the nucleic acid sequences of the present invention.

In accordance with yet another object of the present invention, there is provided a diagnostic assay for detecting a disease or susceptibility to a disease related to a mutation in a nucleic acid sequence of the present invention.

These and other aspects of the present invention should be apparent to those skilled in the art from the teachings herein.

The following drawings are illustrative of embodiments of the invention and are not meant to limit the scope of the invention as encompassed by the claims.

Figure 1:
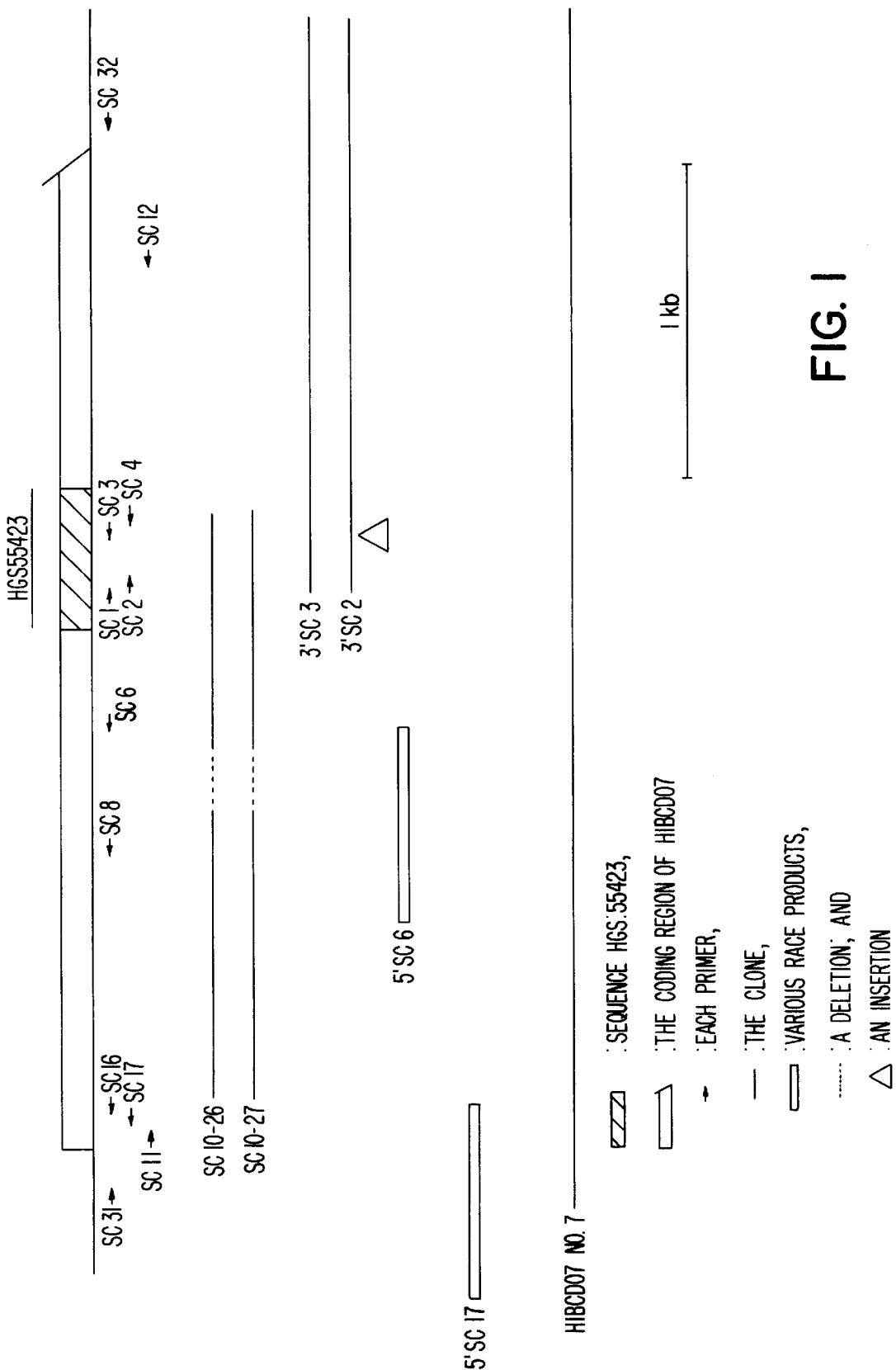
FIG. 1. Schematic representation of various RT-PCR products.

▧▧▧▧:Sequence HGS:55423,

▨▨▨▨:The coding region of HIBCD07,

→:Each primer,

—:The clone,

▭:Various RACE products,

. . . :A deletion; and

Δ:An insertion.

FIG. 2. Sequences of 151 bp insertion site and its vicinity as revealed by 5' RACE. The upper sequence is for SC10–26 and the lower for 5' SC6(SEQ ID NO: 7). The bases are numbered from the 5' end of SC10–26.

FIG. 3. Sequence around the 5' end of HIBCD07 as revealed by 5' RACE.

▼ indicates the 5' end of each 5' RACE product, and ▭indicates the expected initiation codon ATG.

FIGS. 4A, 4B, 4C, 4D, and 4E Sequence of HIBCD07 and corresponding amino acid sequence.

FIG. 5 Northern blot of HIBCD07.

DETAIL DESCRIPTION OF THE INVENTION

In accordance with an aspect of the present invention, there are provided isolated nucleic acids (polynucleotides) which encode for the mature polypeptide having the deduced amino acid sequence of FIGS. 4A, 4B, 4C, 4D, and 4E (SEQ ID NO:2) or for the mature polypeptide encoded by the cDNA of the clone deposited at the American Type Culture Collection, 12301 Parklawn Drive, Rockville, Md. 20852, U.S.A. on Apr. 30, 1996 as *Escherichia coli* XL-1 Blue cells containing HIBDC07 plasmid assigned as ATCC Deposit No. 98039.

A polynucleotide encoding the polypeptide of the present invention was isolated from a cDNA library derived from human placenta and human brain tissues. It is structurally related to the G protein-coupled receptor family. It contains an open reading frame encoding a protein of 1053 amino acid residues. The protein exhibits the highest degree of homology to ERM1 with 27.8% identity and 55.0% similarity over a 305 amino acid stretch. It also has a similar degree of homology to several corticotropin releasing factor receptors (CRF-R's).

Potential ligands to the receptor polypeptide of the present invention include but are not limited to adrenomedullin, amylin, CGRP (calcitonin gene related proteins), anandamide, serotonin, adrenalin and noradrenalin, platelet activating factor, thrombin, C5a and bradykinin, chemokine, and platelet activating factor.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 4A, 4B, 4C, 4D, and 4E (SEQ ID NO:1) or that of the deposited clone or may be a different coding sequence which coding sequence, as a result of the redundancy or degeneracy of the genetic code, encodes the same mature polypeptide as the DNA of FIGS. 4A, 4B, 4C, 4D, and 4E (SEQ ID NO: 1) or the deposited cDNA.

The polynucleotides which encode for the mature polypeptides of FIGS. 4A, 4B, 4C, 4D, and 4E (SEQ ID NO:2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 4A, 4B, 4C, 4D, and 4E (SEQ ID NO:2) or the polypeptide encoded by the cDNA of the deposited clone. The variants of the polynucleotides may be a naturally occurring allelic variant of the polynucleotides or a non-naturally occurring variant of the polynucleotides.

Thus, the present invention includes polynucleotides encoding the same mature polypeptide as shown in FIGS. 4A, 4B, 4C, 4D, and 4E (SEQ ID NO:2) or the same mature polypeptide encoded by the cDNA of the deposited clone as well as variants of such polynucleotides which variants encode for a fragment, derivative or analog of the polypeptide of FIGS. 4A, 4B, 4C, 4D, and 4E (SEQ ID NO:2) or the polypeptide encoded by the cDNA of the deposited clone. Such nucleotide variants include deletion variants, substitution variants and addition or insertion variants.

As hereinabove indicated, the polynucleotides may have a coding sequence which is a naturally occurring allelic variant of the coding sequence shown in FIGS. 4A, 4B, 4C, 4D, and 4E (SEQ ID NO: 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptides.

The polynucleotides may also encode for a soluble form of the receptor polypeptide of the present invention which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length gene and to isolate other genes which have a high sequence similarity to the gene or similar biological activity. Probes of this type preferably have at least 20 or 30 bases and may contain, for example, 50 or more bases. The probe may also be used to identify a cDNA clone corresponding to a fall length transcript and a genomic clone or clones that contain the complete gene of the present invention including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 4A, 4B, 4C, 4D, and 4E (SEQ ID No: 1) or the deposited cDNA(s).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 20 or 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted. This deposit was made under the Budapest Treaty on the International Recognition of the Deposit of Microorganisms. Upon granting of a patent, Applicants will make the deposit available to the public without restriction.

The present invention further relates to a G-protein coupled receptor polypeptide which has the deduced amino acid sequence of FIGS. 4A, 4B, 4C, 4D, and 4E (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 4A, 4B, 4C, 4D, and 4E (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptides of the present invention may be recombinant polypeptides, a natural polypeptides or synthetic polypeptides, preferably recombinant polypeptides.

The fragment, derivative or analog of the polypeptide of FIGS. 4A, 4B, 4C, 4D, and 4E (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the G-protein coupled receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli; Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, 17, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli*, *Bacillus subtilis*, *Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (romega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHOHS293, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinty chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The G-protein coupled receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the G-protein coupled receptor. The expressed receptor is then contacted with a test compound to observe binding, stimulation or inhibition of a functional response.

One such screening procedure involves the use of melanophores which are transfected to express the G-protein coupled receptor of the present invention. Such a screening technique is described in PCT WO 92/01810 published February 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptor on the one hand and which can inhibit the function of a G-protein coupled receptor on the other hand.

For example, compounds which activate the G-protein coupled receptor may be employed for therapeutic purposes, such as the treatment of asthma, Parkinson's disease, acute heart failure, hypotention (or hypertension) urinary retention, and osteoporosis.

In general, compounds which inhibit activation of the G-protein coupled receptor may be employed for a variety of therapeutic purposes, for example, for the treatment of hypertension (or hypotension), angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, among others. Compounds which inhibit G-protein coupled receptors have also been useful in reversing endogenous anorexia and in the control of bulimia.

An antibody may antagonize a G-protein coupled receptor of the present invention, or in some cases an oligopeptide, which bind to the G-protein coupled receptor but does not elicit a second messenger response such that the activity of the G-protein coupled receptors is prevented. Antibodies include anti-idiotypic antibodies which recognize unique determinants generally associated with the antigen-binding site of an antibody. Potential antagonist compounds also include proteins which are closely related to the ligand of the G-protein coupled receptors, i.e. a fragment of the ligand, which have lost biological function and when binding to the G-protein coupled receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

A small molecule which binds to the G-protein coupled receptor, making it inaccessible to ligands such that normal biological activity is prevented, for example small peptides or peptide-like molecules, may also be used to inhibit activation of the receptor polypeptide of the present invention.

A soluble form of the G-protein coupled receptor, e.g. a fragment of the receptors, may be used to inhibit activation of the receptor by binding to the ligand to a polypeptide of the present invention and preventing the ligand from interacting with membrane bound G-protein coupled receptors.

This invention additionally provides a method of treating an abnormal condition related to an excess of G-protein coupled receptor activity which comprises administering to a subject the inhibitor compounds as hereinabove described along with a pharmaceutically acceptable carrier in an amount effective to inhibit activation by blocking binding of ligands to the G-protein coupled receptors, or by inhibiting a second signal, and thereby alleviating the abnormal conditions.

The invention also provides a method of treating abnormal conditions related to an under-expression of G-protein coupled receptor activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of the G-protein coupled receptor, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions described herein may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein coupled receptor polypeptides, and compounds which activate or inhibit such polypetides are also compounds which may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human imunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thyrnidine kinase promoter; retroviral LTRs (including the modified retroviral LTRs hereinabove described); the b-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, y-2, y-AM, PA12, T19–14X, VT-19–17-H2, yCRE, yCRIP, GP+E-86, GP+envAm12, and DAN cell lines as described in Miller, *Human Gene Therapy,* Vol. 1, pg. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles, then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor of the present invention can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor.

This invention further provides a method of screening drugs to identify drugs which specifically interact with, and bind to, the human G-protein coupled receptors of the present invention on the surface of a cell which comprises contacting a mammalian cell comprising an isolated DNA molecule encoding the G-protein coupled receptor with a plurality of drugs, determining those drugs which bind to the mammalian cell, and thereby identifying drugs which specifically interact with and bind to a human G-protein coupled receptor of the present invention. Such drugs may then be used therapeutically to either activate or inhibit activation of the receptors of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe of the present invention capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor genes as part of a diagnostic assay for detecting diseases and abnormalities or susceptibility to diseases and abnormalities related to the presence of mutations in the nucleic acid sequences which encode the receptor polypeptides of the present invention. Such diseases, by way of example, are related to cell transformation, such as tumors and cancers and various cardiovascular disorders, including hyper- and hypotention.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al, Nature, 324:163–166 (1986)) prior to analysis. RNA or cDNA may also be used for the same purpose. As an example, PCR primers complementary to the nucleic acid encoding the G-protein coupled receptor proteins can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Sequence differences between the reference gene and gene having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al, PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptide, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkiris University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 mg of approximately equimolar amounts of the DNA fragments to be ligated.

Unless otherwise stated, transformation is performed as described in the method of Graham, F. and Van der Eb, A., Virology, 52:456–457 (1973).

The followings examples are presented only for illustrative purpose, and should not be construed in any way limiting the scope of this invention.

EXAMPLE 1

Cloning of cDNA containing full coding region for receptor protein from human poly (A)$^+$ RNA and sequence analysis Example 1-1

Cloning, by PCR of cDNA for receptor protein from human placenta-derived cDNA library and sequence analysis In order to obtain the full coding region for the receptor protein encoded by HGS:55423, preparation thereof was performed from a human placenta lgt11 cDNA library (Clontech).

First, based on the sequence of HGS:55423, the following four primers were synthesized:

SC1 5'-CCGTCATTGTCCTGGTGAACATGCTC-3' (SEQUENCE ID NO: 3)
SC2 5'-ATCATCGTCTFCAACAAGTTCATGGC-3' (SEQUENCE ID NO: 4)
SC3 5'-AGTTGAAGACAGCAAAGAGGGCCTGG-3' (SEQUENCE ID NO: 5)
SC4 5'-AGGAAGCAGTGCACAGCAGTGATGAC-3' (SEQUENCE ID NO: 6)

The PCR was carried out in the following manner.

First, the human placenta cDNA library was denatured by incubating at 95° C. for 10 minutes, followed by quenching with ice. Then, this sample was centrifuged (15000 rpm, 5 minutes) and the supernatant was recovered. In each PCR procedure, 1×10$^6$ pfu was used 15 as a template. Then, the first PCR was carried out using a forward or reverse primer specific to lgt11 (Takara), in combination with SC4 (SEQUENCE ID NO: 6) for amplification on this side and with SC1 (SEQUENCE ID NO: 3) for 3' side amplification; Ex Taq (Takara) was used as a DNA polymease. The conditions were 30 seconds at 95° C., 60 seconds at 60° C. and 180 seconds at 72° C., for 30 cycles. The volume was 50 µl.

Then the second PCR was carried out under the same conditions as mentioned above except that 1 µl of the first PCR mixture was used as a template and that SC3 (SEQUENCE ID NO: 5) was added for 5' side amplification and SC2 (SEQUENCE ID NO: 4) for 3' side amplification respectively in lieu of the primers SC4 (SEQUENCE ID NO: 6) and SC1 (SEQUENCE ID NO: 3) mentioned above. A one-fifth portion of the PCR product was subjected to agarose gel electrophoresis, followed by ethidium bromide staining. All bands that had appeared were recovered using SUPREC™ (Takara). These DNAs were subcloned into the pCRII vector using a TA cloning kit (Invitrogen) and used to transform Escherichia coli JM109. As a result of sequence analysis of the plasmids harbored in the transformnants, two clones, SC10-26 and SC10-27, seemingly coding for a 5' upstream region of HGS:55423 were obtained. SC10-26 and SC10-27 contains a cDNA of about 1.8 kb as amplified from the placental cDNA library by PCR (FIG. 1).

Example 1-2

Cloning, by 3' RACE. of receptor protein-encoding cDNA from human placenta-derived poly(A)$^+$-RNA and sequence analysis Since the above PCR failed to give any 3' downstream region of HGS:55423 from the lgt11 library, an attempt was made to obtain such region by 3' RACE.

The 3' RACE was carried out in accordance with the manual attached to a 3' RACE kit (Gibco BRL). More specifically, starting with 1 µg of human placental poly (A)$^+$ RNA (Clontech), cDNA was synthesized using the adaptor primer attached to the 3' RACE kit. Then, a one-tenth portion of the cDNA prepared by using the adaptor primer and the above-mentioned primer SC1 (SEQUENCE ID NO: 3) was used for the first PCR at 95° C. for 30 seconds, at 65° C. for 60 seconds, at 72° C. for 180 seconds, for 25 cycles for which Ex Taq (Takara) was used. Then, a one-fiftieth portion of the reaction mixture was used for the second PCR, which was carried out under the same conditions and the primer SC2 (SEQUENCE ID NO: 4) and adaptor primer mentioned above, followed by ethidium bromide staining and recovery of a resulting DNA band of about 1.3 kb using SUPREC™-01 (Takara). This DNA was subcloned into the vector pCRII using a TA cloning kit, for transforming Escherichia coli JM109. As a result of analysis of the plasmid harbored therein, clones 3' SC3 (SEQUENCE ID NO: 5) and 3' SC2, (SEQUENCE ID NO: 4) seemingly coding for a 3' downstream region of HGS:55423 were obtained (FIG. 1). 3' SC3 (SEQUENCE ID NO: 5) and 3' SC2 (SEQUENCE ID NO: 4) contains a cDNA about 1.3 kb in length as amplified by 3' RACE. In 3' SC2, (SEQUENCE ID NO: 4) the insertion of about 100 bp can be confined in the middle of the sequence of HGS:55423.

Based on the base sequences of the clones SC10-26 and SC10-27 supposedly containing an N terminal side sequence and the clones 3' SC3 (SEQUENCE ID NO: 5) and 3' SC2 (SEQUENCE ID NO: 4) supposedly containing a C terminal side sequence, the base sequence of the translational region and its vicinity of the receptor protein encoded by the cDNA contained in HGS:55423, as shown in FIG. 1, was estimated. More specifically, the reaction was carried out using the primers used for PCR and the primers synthesized for the base sequence and a Dyedeoxy terminator cycle sequencing kit (AB1), followed by decoding using a fluorescent automatic sequencer. The DNA sequence obtained was analyzed using Bright DNASIS (Hitachi System Engineering). The amino acid sequence deduced from the thus-determined base sequence indicated that the protein expected from HGS:55423 lacks the third transmembrane domain and the preceding region, namely the first, second and third transmembrane domains in the direction toward the 5' side, suggesting the possibility that said protein might not be a receptor comprising seven transmembrane domains. Therefore, 5' RACE was performed from around the fifth transmembrane domain for confirming whether the third transmembrane domain and the preceding ones are indeed present or not.

Example 1-3

Cloning by 5' RACE of cDNA containing third transmembrane domain of receptor protein from human placenta and human brain-derived poly (A)+ RNA and base sequence analysis First, the following primer was synthesized based on the base sequence of the coding region of HGS:55423 that had already been revealed:

SC6 5'GAAGACGATGATTCCGATGAGCATG-3' (SEQUENCE D NO: 7)

5' RACE was carried out in accordance with the manual attached to Clontech's 5' Amplifmder™ RACE kit. More specifically, cDNA synthesis was effected from 2 µg each of human placenta- and brain-derived poly (A)+ RNA (Clontech) using the above-mentioned primer SC4, (SEQUENCE ID NO: 6) followed by ligation of the anchor primer attached to the 5' RACE kit. A one-two hundredth of the product was subjected to PCR using the anchor primer and the above-mentioned primer SC3 (SEQUENCE ID NO: 5) at 95° C. for 30 seconds, at 65° C. for 60 seconds and at 72° C. for 150 seconds, for 30 cycles. Further, a one-fiftieth portion of the PCR reaction mixture was subjected to nested PCR under the same conditions except that the primer SC6 (SEQUENCE ID NO: 7) was used in lieu of the primer SC3 (SEQUENCE ID NO: 5). A one-fifth portion of the reaction mixture was subjected to agarose gel electrophoresis, followed by ethidium bromide staining. The bands that had appeared were recovered and, after TA cloning, used to transform *Escherichia. coli* JM109. Eleven clones thus obtained were analyzed for base sequence. As a result, it was found that one of the clones contained the sequences as SC10-26 and SC10-27, three clones had a sequence quite different in the region preceding the position of the 1450th bp, and seven clones (5' SC6(SEQUENCE ID NO: 7)) had an insertion of 151 bp at the site of the 1454th bp (FIG. 2). The base sequence of the inserted portion and a vicinity thereof is shown in FIGS. 4A, 4B, 4C, 4D, and 4E. When the sequences of SC10-26 and SC 10-27, the sequence of the 151 bp insert and, further, the sequence of 3' SC3 (SEQUENCE ID NO: 5) are joined together, the 1st to 7th transmembrane domains of the 7 transmembrane domain-containing receptor can indeed be confirmed.

Example 1-4

Estimation, by 5' RACE, of N-terminal ATG, initiation codon, HGS:55423

In the sequences obtained in Examples 1-1 to 1-3, no termination codon can be confirmed in frame upstream from the estimated ATG. Therefore, 5' RACE was carried out for definitely locating the translation initiation codon ATG.

First, based on the sequences obtained in Examples 1-1 to 1-3, the following three primers were synthesized:

SC8 5'-AAGGTGGACAGGTGCTGGCACTG-3' (SEQUENCE ID NO: 8)

SC16 5'-GGCACTTGTTGTAGATGATCTCGCCAGC-3' (SEQUENCE ID NO: 9)

SC17 5'-CTGCCTTCTTCCACGTCATCAGCATCACG-3' (SEQUENCE ID NO. 10)

5' RACE was carried out in accordance with the manual of Clontech's 5' AmpliFinder RACE kit.

More specifically, cDNA was first synthesized from 2 µg of human brain poly (A)+ RNA using the above primer SC8 (SEQUENCE ID NO: 8) or SC16, (SEQUENCE ID NO: 9) followed by litigation of the anchor primer attached to the 5' RACE kit. A one-two hundredth portion of the reaction mixture was subjected, together with the anchor primer and the above primer SC16 (SEQUENCE ID NO: 9) or SC17, (SEQUENCE ID NO: 10) to PCR using Ex Taq polymerase at 95° C. for 30 seconds, at 65° C. for 60 seconds and at 72° C. for 120 seconds, for 30 cycles. Further, a one-fiftieth portion of the first PCR mixture was subjected to the second PCR under the same conditions using SC17 (SEQUENCE ID NO: 10) in lieu of SC16 (SEQUENCE ID NO: 9). A one-fifth portion of each reaction mixture was subjected to agarose gel electrophoresis, followed by ethidium bromide staining. The resultant bands varying in size were recovered and, after TA cloning, used for transforming *Escherichia Coli* JM109. Eleven clones (5' SC17(SEQUENCE ID NO: 10)) thus obtained were analyzed for base sequence. The 5' end of these eleven clones occurred at the position ▼ shown in FIG. 3. Based on the above result, the ATG enclosed in □ (184 bp in FIG. 3) was tentatively estimated to be the translation initiation codon.

Example 1-5

Reacquisition, by RT-PCR, of translational region of HGS:55423(HIBCD07) from human brain poly (A)+RNA The full length of HOBCD07 was obtained from human brain poly (A)+ RNA by RT-PCR.

First, the following two primers were prepared for the 5' upstream of the translation initiation codon and the 3' downstream of the termination codon, based on the base sequence of HIBCD07 that already been revealed:

SC31
5'-GTCGACGTGTGACACAGGCTGGCAGCGCCGCTTC-3' (SEQUENCE ID NO: 11)

SC32
5'-TGGCTCCTGGGTAGTTCCAAAGTGGAGTGTG-3' (SEQUENCE ID NO: 12)

Complementary DNA synthesis was effected by adding random DNA hexamers (BRL) to 5 µg of human brain poly (A)+ RNA and using Superscript II reverse transcriptase (BRL) and the buffer and other reagents attached thereto. After the reaction, the product was treated at 90° C. for 10 minutes and then subjected to ethanol precipitation. The precipitate was dissolved in 30 µl of TE. The translational region of HMCD07 was amplified using 1 µl of the cDNA solution, together with the above primers SC31 (SEQUENCE ID NO: 11) and SC32 (SEQUENCE ID NO: 12), in accordance with the manual of LA PCR kit (Takara). The DNA obtained was inserted into the pCRII vector using a TA cloning kit for transforming *Escherichia. coli*. Plasmids were extracted from transformants thus obtained and, after identification of the insert fragment, subjected to sequence analysis. As a result, a clone, HIBCD07 (No. 7)/JM109, was obtained with which it was confirmed that the cDNA was free from any insertion or deletion, any PCR error or any other defect (FIG. 1). The base sequence thereof is shown in FIG. 4A, 4B, 4C, 4D, and 4E.

Various products resulting from the RACE of HIBCD07 are also shown schematically in FIG. 1.

EXAMPLE 2
Northern blot analysis of HIBCD07

Northern blot was carried out to confirm the expression of the receptor mRNA encoded by HIBCD07 in human tissues. Human MTN Blot I and II (Clontech) were used as nothern blot filters. For use as probes for hybridization, the primers shown below were synthesized based on the information on cDNA as obtained in Example 1 and then amplified by PCR, the DNA fragments obtained were subjected to TA cloning and, after sequence confirmation, DNA fragments about 2 bk in size were produced by cleavage with EcoRI. The fragments were recovered and labeled by allowing them to take up [$^{32}$P]dCTP (du Pont) using a random prime labeling kit (Amersham). The sequences of the primers synthesized:

SC11
5'AAGCCTTGTAGTGAGAAGAGGTGTCCAGCC-3'
(SEQUENCE ID NO: 13)

SC12
5'AGGCTGCCATGGGCACCAGGATGTTCCCAG-3'
(SEQUENCE ID NO: 14)

The hybridization and wash were performed in accordance with the manual of MTN Blot and X-ray film (X-AR) exposure was made at −80° C. for 9days.

As shown in FIG. 5 positive signals were detected in all tissues examined so far by the Northern Blot analysis. Of these tissues, strong signals were detected especially in the brain, thymus, and heart.

What is claimed is:

1. An isolated polypeptide selected from the group consisting of (i) a polypeptide having the deduced amino acid sequence of SEQ ID NO:2; and (ii) a polypeptide encoded by the cDNA of ATCC Deposit No. 98039.

2. The polypeptide of claim 1 wherein the polypeptide has the amino acid sequence set forth in SEQ ID NO:2.

3. An isolated polypeptide comprising an amino acid sequence of at least 30 contiguous amino acids from the amino acid sequence as set forth in SEQ ID NO: 2.

4. The isolated polypeptide of claim 3 comprising an amino acid sequence of at least 50 contiguous amino acids from the amino acid sequence as set forth in SEQ ID NO: 2.

5. The isolated polypeptide of claim 3 comprising an amino acid sequence of at least 100 contiguous amino acids from the amino acid sequence as set forth in SEQ ID NO: 2.

6. The isolated polypeptide of claim 3 comprising an amino acid sequence of at least 200 contiguous amino acids from the amino acid sequence as set forth in SEQ ID NO: 2.

7. The isolated polypeptide of claim 3 comprising an amino acid sequence of at least 400 contiguous amino acids from the amino acid sequence as set forth in SEQ ID NO: 2.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 3271 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
TGTGACACAG GCTGGCAGCG CCGCTTCCGC ATGTGCCAGG CCACGGGCAC GCAGGGCTAC      60

CCCTGCGAGG GCACCGGAGA GGAGGTGAAG CCTTGTAGTG AGAAGAGGTG TCCAGCCTTC     120

CATGAGATGT GCAGGGATGA GTACGTGATG CTGATGACGT GGAAGAAGGC AGCTGCTGGC     180

GAGATCATCT ACAACAAGTG CCCCCCGAAT GCCTCAGGGT CTGCCAGCCG CCGCTGTCTC     240

CTCAGTGCCC AAGGCGTGGC GTACTGGGGG CTGCCCAGCT TTGCTCGCTG CATCTCCCAT     300

GAGTACCGCT ACCTGTATCT GTCACTTAGG GAGCACCTGG CCAAGGGGCA GCGCATGCTG     360

GCAGGCGAGG GCATGTCGCA GGTGGTGCGC AGCCTGCAGG AGCTACTGGC CCGGCGCACC     420

TACTATAGTG GGGACCTGCT CTTCTCTGTG GACATTCTGA GGAATGTCAC TGACACCTTT     480

AAGAGGGCCA CCTACGTGCC CTCGGCTGAT GATGTGCAGC GCTTCTTCCA GGTGGTGAGC     540

TTCATGGTGG ATGCGGAAAA CAAGGAGAAG TGGGACGATG CTCAGCAGGT GTCCCCTGGC     600

TCTGTGCACC TGCTCCGTGT CGTGGAGGAC TTCATTCACC TGGTGGGCGA TGCTCTCAAG     660

GCCTTCCAGA GCTCTCTGAT TGTCACAGAT AATCTAGTGA TCAGCATTCA GCGAGAGCCC     720

GTCTCAGCTG TGTCCAGTGA CATCACGTTC CCCATGCGGG GCCGCCGGGG CATGAAGGAC     780

TGGGTGCGGC ACTCAGAGGA CCGCCTCTTC CTGCCCAAGG AGGTGCTCAG CCTCTCCTCC     840

CCAGGGAAGC CAGCCACATC TGGGGCAGCA GGCAGCCCTG GCAGGGGGAG GGGCCCAGGA     900

ACGGTGCCTC CTGGCCCAGG CCACTCCCAC CAGCGCCTCC TCCCAGCAGA CCCTGATGAG     960

TCCTCCTACT TTGTGATCGG TGCTGTACTC TACCGCACCC TTGGCCTCAT CCTGCCGCCT    1020

CCCAGGCCCC CGCTGGCCGT CACATCCCGG GTGATGACAG TGACTGTGCG CCCCCCTACC    1080

CAGCCTCCAG CTGAGCCCCT CATCACTGTG GAGCTCTCCT ACATCATCAA TGGGACCACG    1140

GATCCCCATT GCGCCAGCTG GGACTACTCC AGAGCAGATG CCAGCTCAGG AGACTGGGAC    1200
```

```
ACTGAAAATT GCCAGACCCT GGAGACCCAG GCAGCTCACA CCCGCTGCCA GTGCCAGCAC    1260

CTGTCCACCT TTGCTGTACT AGCCCAGCCG CCCAAGGACC TGACCCTGGA GCTGGCGGGC    1320

TCCCCCTCGG TCCCCCTGGT GATCGGCTGT GCAGTGTCGT GCATGGCGCT GCTCACCCTG    1380

CTCGCCATCT ATGCCGCCTT TTGGAGGTTC ATAAAATCTG AACGCTCCAT CATCTTGCTG    1440

AACTTCTGCC TGTCCATCTT GGCATCCAAC ATCCTGATCC TCGTGGGCCA GTCCCGGGTG    1500

CTGAGCAAGG GCGTGTGCAC CATGACGGCT GCCTTCCTGC ACTTCTTCTT TCTCTCCTCC    1560

TTTTGCTGGG TGCTTACCGA GGCCTGGCAG TCCTACCTGG CTGTCATTGG GCGGATGCGC    1620

ACCCGCCTCG TTCGCAAGCG CTTCCTCTGC CTGGGCTGGG GTCTGCCTGC CCTGGTGGTG    1680

GCCGTGTCTG TTGGCTTTAC CCGAACGAAA GGATACGGTA CATCCAGCTA CTGCTGGCTC    1740

TCCCTGGAGG GCGGCCTGCT CTACGCCTTT GTGGGCCCTG CAGCCGTCAT TGTCCTGGTG    1800

AACATGCTCA TCGGAATCAT CGTCTTCAAC AAGCTCATGG CACGTGATGG CATTTCCGAC    1860

AAATCCAAGA AGCAGAGGGC CGGGGCCTCA CTCTGGAGCT CCTGCGTGGT GCTGCCCCTG    1920

CTGGCGCTCA CCTGGATGTC TGCCGTCCTG GCTATGACAG ACCGCCGTTC CGTCCTCTTC    1980

CAGGCCCTCT TTGCTGTCTT CAACTCCGCG CAGGGCTTTG TCATCACTGC TGTGCACTGC    2040

TTCCTGCGCC GAGAGGTCCA GGATGTGGTG AAGTGCCAGA TGGGGGTGTG CCGGGCTGAT    2100

GAGAGCGAAG ACTCCCCTGA CTCGTGTAAG AACGGGCAGC TGCAGATCCT GTCAGACTTT    2160

GAAAAGGATG TGGATCTGGC TTGTCAAACA GTGCTGTTCA AGGAGGTCAA CACTTGCAAC    2220

CCGTCCACCA TCACGGGCAC ACTATCCCGC CTGTCCCTGG ATGAGGATGA GGAGCCCAAG    2280

TCCTGCCTCG TGGGCCCTGA GGGCAGCCTC AGCTTCTCAC CACTGCCTGG GAATATCCTG    2340

GTGCCCATGG CAGCCTCACC AGGGCTGGGG GAGCCTCCGC CCCCACAGGA GGCCAACCCT    2400

GTTTACATGT GTGGGGAGGG TGGCCTGCGG CAGCTGGACC TCACATGGCT GCGGCCCACT    2460

GAGCCAGGCT CTGAGGGAGA CTACATGGTG CTGCCCCGGC GGACTTTGAG CCTGCAGCCT    2520

GGCGGTGGGG GTGGAGGTGG TGAGGATGCC CCCAGGGCCC GGCCCGAGGG GACCCCCCGG    2580

CGAGCTGCCA AGACAGTGGC CCACACTGAA GGCTACCCCA GCTTCCTGTC CGTGGACCAC    2640

TCGGGCCTGG GGCTGGGCCC TGCCTATGGA TCTCTCCAGA ATCCCTATGG AATGACCTTC    2700

CAACCGCCAC CGCCGACACC CAGCGCCCGC CAAGTGCCCG AGCCAGGGGA GCGCAGCCGG    2760

ACCATGCCTC GCACCGTGCC CGGCTCTACC ATGAAGATGG GCTCCCTGGA GCGAAAGAAA    2820

TTACGGTATT CAGACCTGGA CTTTGAGAAG GTGATGCACA CCCGGAAACG GCATTCAGAA    2880

CTCTACCACG AGCTCAACCA GAAGTTCCAC ACTTTCGACC GCTACCGCAG CCAGTCCACG    2940

GCCAAGAGGG AGAAGCGGTG GAGTGTGTCC TCGGGTGGGG CGGCCGAGCG GAGCGTGTGC    3000

ACCGATAAGC CCAGCCCTGG GGAGCGCCCC AGCTTGTCCC AACATCGGCG CCATCAGAGC    3060

TGGAGCACCT TCAAATCTAT GACACTGGGC TCGCTGCCCC CCAAGCCCCG AGAACGGCTG    3120

ACTCTGCACC GGGCAGCAGC CTGGGAGCCC ACAGAACCAC CGGATGGTGA CTTCCAGACA    3180

GAGGTGTGAG TGCACGCTG GACTGCCCAC TGCATATAAA TATATATATC TCTCTATTTT    3240

CACACTCCAC TTTGGAACTA CCCAGGAGCC A                                  3271

(2) INFORMATION FOR SEQ ID NO:2:

(i) SEQUENCE CHARACTERISTICS:
        (A) LENGTH: 1052 amino acids
        (B) TYPE: amino acid
        (C) STRANDEDNESS: single
        (D) TOPOLOGY: linear
```

(ii) MOLECULE TYPE: protein (xi) SEQUENCE DESCRIPTION: SEQ ID NO:2:

```
Met Cys Gln Ala Thr Gly Thr Gln Gly Tyr Pro Cys Glu Gly Thr Gly
 1               5                  10                  15

Glu Glu Val Lys Pro Cys Ser Glu Lys Arg Cys Pro Ala Phe His Glu
            20                  25                  30

Met Cys Arg Asp Glu Tyr Val Met Leu Met Thr Trp Lys Lys Ala Ala
        35                  40                  45

Ala Gly Glu Ile Ile Tyr Asn Lys Cys Pro Pro Asn Ala Ser Gly Ser
50                  55                  60

Ala Ser Arg Arg Cys Leu Leu Ser Ala Gln Gly Val Ala Tyr Trp Gly
65                  70                  75                  80

Leu Pro Ser Phe Ala Arg Cys Ile Ser His Glu Tyr Arg Tyr Leu Tyr
                85                  90                  95

Leu Ser Leu Arg Glu His Leu Ala Lys Gly Gln Arg Met Leu Ala Gly
            100                 105                 110

Glu Gly Met Ser Gln Val Val Arg Ser Leu Gln Glu Leu Leu Ala Arg
        115                 120                 125

Arg Thr Tyr Tyr Ser Gly Asp Leu Leu Phe Ser Val Asp Ile Leu Arg
130                 135                 140

Asn Val Thr Asp Thr Phe Lys Arg Ala Thr Tyr Val Pro Ser Ala Asp
145                 150                 155                 160

Asp Val Gln Arg Phe Phe Gln Val Val Ser Phe Met Val Asp Ala Glu
                165                 170                 175

Asn Lys Glu Lys Trp Asp Asp Ala Gln Gln Val Ser Pro Gly Ser Val
            180                 185                 190

His Leu Leu Arg Val Val Glu Asp Phe Ile His Leu Val Gly Asp Ala
        195                 200                 205

Leu Lys Ala Phe Gln Ser Ser Leu Ile Val Thr Asp Asn Leu Val Ile
210                 215                 220

Ser Ile Gln Arg Glu Pro Val Ser Ala Val Ser Ser Asp Ile Thr Phe
225                 230                 235                 240

Pro Met Arg Gly Arg Arg Gly Met Lys Asp Trp Val Arg His Ser Glu
                245                 250                 255

Asp Arg Leu Phe Leu Pro Lys Glu Val Leu Ser Leu Ser Ser Pro Gly
            260                 265                 270

Lys Pro Ala Thr Ser Gly Ala Ala Gly Ser Pro Gly Arg Gly Arg Gly
        275                 280                 285

Pro Gly Thr Val Pro Pro Gly Pro Gly His Ser His Gln Arg Leu Leu
290                 295                 300

Pro Ala Asp Pro Asp Glu Ser Ser Tyr Phe Val Ile Gly Ala Val Leu
305                 310                 315                 320

Tyr Arg Thr Leu Gly Leu Ile Leu Pro Pro Arg Pro Pro Leu Ala
                325                 330                 335

Val Thr Ser Arg Val Met Thr Val Thr Val Arg Pro Thr Gln Pro
            340                 345                 350

Pro Ala Glu Pro Leu Ile Thr Val Glu Leu Ser Tyr Ile Ile Asn Gly
        355                 360                 365

Thr Thr Asp Pro His Cys Ala Ser Trp Asp Tyr Ser Arg Ala Asp Ala
370                 375                 380

Ser Ser Gly Asp Trp Asp Thr Glu Asn Cys Gln Thr Leu Glu Thr Gln
385                 390                 395                 400
```

-continued

```
Ala Ala His Thr Arg Cys Gln Cys Gln His Leu Ser Thr Phe Ala Val
            405                 410                 415

Leu Ala Gln Pro Pro Lys Asp Leu Thr Leu Glu Leu Ala Gly Ser Pro
            420                 425                 430

Ser Val Pro Leu Val Ile Gly Cys Ala Val Ser Cys Met Ala Leu Leu
            435                 440                 445

Thr Leu Leu Ala Ile Tyr Ala Ala Phe Trp Arg Phe Ile Lys Ser Glu
450                 455                 460

Arg Ser Ile Ile Leu Leu Asn Phe Cys Leu Ser Ile Leu Ala Ser Asn
465                 470                 475                 480

Ile Leu Ile Leu Val Gly Gln Ser Arg Val Leu Ser Lys Gly Val Cys
            485                 490                 495

Thr Met Thr Ala Ala Phe Leu His Phe Phe Leu Ser Ser Phe Cys
            500                 505                 510

Trp Val Leu Thr Glu Ala Trp Gln Ser Tyr Leu Ala Val Ile Gly Arg
            515                 520                 525

Met Arg Thr Arg Leu Val Arg Lys Arg Phe Leu Cys Leu Gly Trp Gly
            530                 535                 540

Leu Pro Ala Leu Val Val Ala Val Ser Val Gly Phe Thr Arg Thr Lys
545                 550                 555                 560

Gly Tyr Gly Thr Ser Ser Tyr Cys Trp Leu Ser Leu Glu Gly Gly Leu
            565                 570                 575

Leu Tyr Ala Phe Val Gly Pro Ala Ala Val Ile Val Leu Val Asn Met
            580                 585                 590

Leu Ile Gly Ile Ile Val Phe Asn Lys Leu Met Ala Arg Asp Gly Ile
            595                 600                 605

Ser Asp Lys Ser Lys Lys Gln Arg Ala Gly Ala Ser Leu Trp Ser Ser
            610                 615                 620

Cys Val Val Leu Pro Leu Leu Ala Leu Thr Trp Met Ser Ala Val Leu
625                 630                 635                 640

Ala Met Thr Asp Arg Arg Ser Val Leu Phe Gln Ala Leu Phe Ala Val
            645                 650                 655

Phe Asn Ser Ala Gln Gly Phe Val Ile Thr Ala Val His Cys Phe Leu
            660                 665                 670

Arg Arg Glu Val Gln Asp Val Val Lys Cys Gln Met Gly Val Cys Arg
            675                 680                 685

Ala Asp Glu Ser Glu Asp Ser Pro Asp Ser Cys Lys Asn Gly Gln Leu
            690                 695                 700

Gln Ile Leu Ser Asp Phe Glu Lys Asp Val Asp Leu Ala Cys Gln Thr
705                 710                 715                 720

Val Leu Phe Lys Glu Val Asn Thr Cys Asn Pro Ser Thr Ile Thr Gly
            725                 730                 735

Thr Leu Ser Arg Leu Ser Leu Asp Glu Asp Glu Glu Pro Lys Ser Cys
            740                 745                 750

Leu Val Gly Pro Glu Gly Ser Leu Ser Phe Ser Pro Leu Pro Gly Asn
            755                 760                 765

Ile Leu Val Pro Met Ala Ala Ser Pro Gly Leu Gly Glu Pro Pro
770                 775                 780

Pro Gln Glu Ala Asn Pro Val Tyr Met Cys Gly Glu Gly Gly Leu Arg
785                 790                 795                 800

Gln Leu Asp Leu Thr Trp Leu Arg Pro Thr Glu Pro Gly Ser Glu Gly
            805                 810                 815

Asp Tyr Met Val Leu Pro Arg Arg Thr Leu Ser Leu Gln Pro Gly Gly
```

-continued

```
                       820                 825                 830
Gly Gly Gly Gly Glu Asp Ala Pro Arg Ala Arg Pro Glu Gly Thr
            835                 840                 845

Pro Arg Arg Ala Ala Lys Thr Val Ala His Thr Glu Gly Tyr Pro Ser
    850                 855                 860

Phe Leu Ser Val Asp His Ser Gly Leu Gly Leu Gly Pro Ala Tyr Gly
865                 870                 875                 880

Ser Leu Gln Asn Pro Tyr Gly Met Thr Phe Gln Pro Pro Pro Thr
                885                 890                 895

Pro Ser Ala Arg Gln Val Pro Glu Pro Gly Glu Arg Ser Arg Thr Met
            900                 905                 910

Pro Arg Thr Val Pro Gly Ser Thr Met Lys Met Gly Ser Leu Glu Arg
        915                 920                 925

Lys Lys Leu Arg Tyr Ser Asp Leu Asp Phe Glu Lys Val Met His Thr
    930                 935                 940

Arg Lys Arg His Ser Glu Leu Tyr His Glu Leu Asn Gln Lys Phe His
945                 950                 955                 960

Thr Phe Asp Arg Tyr Arg Ser Gln Ser Thr Ala Lys Arg Glu Lys Arg
                965                 970                 975

Trp Ser Val Ser Ser Gly Gly Ala Ala Glu Arg Ser Val Cys Thr Asp
            980                 985                 990

Lys Pro Ser Pro Gly Glu Arg Pro Ser Leu Ser Gln His Arg Arg His
        995                 1000                1005

Gln Ser Trp Ser Thr Phe Lys Ser Met Thr Leu Gly Ser Leu Pro Pro
    1010                1015                1020

Lys Pro Arg Glu Arg Leu Thr Leu His Arg Ala Ala Ala Trp Glu Pro
025                 1030                1035                1040

Thr Glu Pro Pro Asp Gly Asp Phe Gln Thr Glu Val
                1045                1050

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCGTCATTGT CCTGGTGAAC ATGCTC                                              26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATCATCGTCT TCAACAAGTT CATGGC                                              26

(2) INFORMATION FOR SEQ ID NO:5:

(i) SEQUENCE CHARACTERISTICS:
        (A) LENGTH: 26 base pairs
```

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGTTGAAGAC AGCAAAGAGG GCCTGG                                               26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGGAAGCAGT GCACAGCAGT GATGAC                                               26

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GAAGACGATG ATTCCGATGA GCATG                                                25

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AAGGTGGACA GGTGCTGGCA CTG                                                  23

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGCACTTGTT GTAGATGATC TCGCCAGC                                             28

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear
```

```
    (ii) MOLECULE TYPE: cDNA (xi) SEQUENCE DESCRIPTION: SEQ ID NO:10:

CTGCCTTCTT CCACGTCATC AGCATCACG                                        29

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTCGACGTGT GACACAGGCT GGCAGCGCCG CTTC                                  34

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TGGCTCCTGG GTAGTTCCAA AGTGGAGTGT G                                     31

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AAGCCTTGTA GTGAGAAGAG GTGTCCAGCC                                       30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGGCTGCCAT GGGCACCAGG ATGTTCCCAG                                       30
```